(12) United States Patent
Enikov

(10) Patent No.: US 9,155,467 B1
(45) Date of Patent: Oct. 13, 2015

(54) CONTOURED FACIAL MASK WITH MULTIPLE CONTACT PROBES FOR USE WITH TACTILE TONOMETER

(71) Applicant: The Arizona Board of Regents on behalf of The University of Arizona, Tucson, AZ (US)

(72) Inventor: Eniko Todorov Enikov, Tucson, AZ (US)

(73) Assignee: THE ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 228 days.

(21) Appl. No.: 13/712,653

(22) Filed: Dec. 12, 2012

Related U.S. Application Data

(60) Provisional application No. 61/570,150, filed on Dec. 13, 2011.

(51) Int. Cl.
*A61B 3/16* (2006.01)

(52) U.S. Cl.
CPC ........................................ *A61B 3/16* (2013.01)

(58) Field of Classification Search
CPC ........... A61B 3/16; A61B 3/165; A61B 3/152
USPC .................................................. 600/398, 399
See application file for complete search history.

(56) References Cited

U.S. PATENT DOCUMENTS

| | | | | |
|---|---|---|---|---|
| 5,830,139 | A * | 11/1998 | Abreu | 600/405 |
| 7,959,570 | B2 | 6/2011 | Enikov et al. | 600/398 |
| 2003/0078486 | A1* | 4/2003 | Klein et al. | 600/398 |
| 2005/0231686 | A1* | 10/2005 | Rathjen | 351/205 |
| 2007/0019156 | A1* | 1/2007 | Fink | 351/200 |
| 2008/0027304 | A1* | 1/2008 | Pardo et al. | 600/399 |
| 2010/0049447 | A1* | 2/2010 | Peyman et al. | 702/19 |
| 2011/0054291 | A1* | 3/2011 | Enikov et al. | 600/405 |

OTHER PUBLICATIONS

Polyvas et al., "Development of Tactile Eye Stiffness Sensor," Journal of Experimental Mechanics, Sep. 2012 (10 pgs).
Polyvas et al., "Trans-scleral tactile tonometry: An instrumented approach," Medical Engineering & Physics, Sep. 2012 (7 pgs).
Mills, N.J., "Finite Element Models for the viscoelasticity of open-cell polyurethane foam," Cellular Polymers, vol. 25. No. 5, 2006, pp. 293-316 (24 pgs).

* cited by examiner

*Primary Examiner* — Sean Dougherty
*Assistant Examiner* — Daniel Cerioni
(74) *Attorney, Agent, or Firm* — Hayes Soloway P.C.

(57) ABSTRACT

A system for measuring intraocular pressure (IOP) of an eye, comprising a plurality of force sensors that are adapted to contact a surface of an eye, measuring the forces exerted on the force sensors when in contact with the eye surface, and processing the measured forces to determine the 10P of the eye as a function of the measured forces.

19 Claims, 12 Drawing Sheets

CONTOURED FACIAL MASK WITH MULTIPLE CONTACT PROBES FOR USE WITH TACTILE TONOMETER

CROSS-REFERENCE TO RELATED APPLICATIONS

This application claims the benefit of U.S. Provisional Application No. 61/570,150, filed Dec. 13, 2011.

STATEMENT OF GOVERNMENT INTEREST

The invention was made with Government support under contract numbers 0856761 and 115798 awarded by the National Science Foundation. The Government has certain rights in the invention.

FIELD OF THE PRESENT INVENTION

The present invention relates generally to systems and methods for measuring the intraocular pressure, i.e. the fluid pressure within an eye. More particularly, the invention relates to improved systems and methods for measuring intraocular or fluid pressure within an eye.

BACKGROUND OF THE INVENTION

As is well known in the art of ophthalmology, measuring the intraocular pressure (IOP) of the eye is an important indicator of the health of the eye. Elevated IOP has been associated with progressive damage of the optic nerve known as glaucoma, which, if left untreated, may lead to permanent loss of sight.

Various apparatus and techniques have thus been developed to measure IOP. Among the techniques are applanation tonometery, dynamic contour tonometry, transpalpebral diatom tonometry, non-contact tonometry, electronic indentation tonometry, rebound tonometry and digital palpation tonometry.

Applanation tonometry measures approximate intraocular pressure either by the force required to flatten a constant area of the cornea (e.g. Goldmann tonometry) or by the area flattened by a constant force.

In applanation tonometry, a special calibrated disinfected probe attached to a slit lamp biomicroscope is used to flatten the central cornea a fixed amount. Because the probe makes contact with the cornea, a topical anesthetic, such as oxybuprocaine, tetracaine, alcaine, proxymetacaine or paracaine, is introduced onto the surface of the eye in the form of one or a few eye drops. A yellow fluorescein dye is often also used in conjunction with a cobalt blue filter to aid the examiner in determining the IOP.

Goldmann tonometry is considered to be the gold standard in tonometry, as it is the most widely accepted method of determining "approximate" intraocular pressure. However, as is well known in the art, Goldmann tonometry is an inherently imprecise measurement.

Dynamic contour tonometry (DCT) is a measuring technique that employs the) 5 principle of contour matching instead of applanation to eliminate the systematic errors inherent in previous tonometers. These factors include the influence of corneal thickness, rigidity, curvature and elastic properties. DCT is not influenced by mechanical changes, such as those seen in refractive surgery that would otherwise cause error in applanation tonometers.

An exemplar apparatus that employs DCT to measure IOP is the PASCAL Dynamic Contour Tonometer (Ziemer Ophthalmics). The PASCAL uses a miniature pressure sensor embedded within a tonometer tip that is contour-matched to the shape of the cornea. When the sensor is subjected to a change in pressure, the electrical resistance is altered and the PASCAL's computer calculates a change in pressure in accordance with the change in resistance.

The tonometer tip rests on the cornea with a constant appositional force of one gram. This is an important difference from all forms of applanation tonometry wherein the probe force is variable.

In transpalpebral diaton tonometry, a diaton tonometer is employed to measure intraocular pressure through the eyelid. It is typically regarded as a simple and safe method of ophthalmotonometry. Transpalpebral tonometry requires no contact with the cornea, therefore sterilization of the device and topical anesthetic drops are not required.

Non-contact tonometry or air-puff tonometry uses a rapid air pulse to applanate the cornea. Corneal applanation is detected via an electro-optical system. Intraocular pressure is estimated by detecting the force of the air jet at the instance of applanation.

Modern-day non-contact tonometers have been shown to correlate very well with Goldmann tonometry measurements and have thus generally been considered a fast and simple way to screen for high IOP. Further, since non-contact tonometry is accomplished without the instrument contacting the cornea the potential for disease transmission is reduced.

Electronic indentation tonometry employs a Tono-Pen, i.e. a portable electronic, digital pen-like instrument that determines IOP by making contact with the cornea. Electronic indentation tonometry is especially useful for very young children, patients unable to reach a slit lamp due to disability, patients who are uncooperative during applanation tonometry, or patients with cornea disease in whom contact tonometry cannot be accurately performed.

In palpation tonometry, also known as digital palpation tonometry, measuring intraocular pressure is performed by gently pressing the fingertips of both index fingers onto the upper part of the bulbus through the eyelid. This technique requires medical experience and results in an estimation of the level of intraocular pressure based on the skills of the ophthalmologist.

A major drawback associated with each of the noted techniques is that each technique requires professional assistance to measure IOP.

A further drawback associated with each of the noted techniques is the need for topical anesthesia and complex instrumentation to measure IOP, which makes multiple daily measurements impractical.

It would thus be desirable to provide improved systems and methods for measuring IOP that overcome the disadvantages and drawbacks associated with conventional systems and methods for measuring IOP.

As has been demonstrated by the inventor earlier in publications [1], [2], and disclosed in U.S. Pat. No. 7,959,570 B2 [3], using a multitude of force sensors, it is possible to infer the intraocular pressure of the eye by measuring the forces obtained from such sensors during gradual indentation of the eye with these probes.

It has further been shown in [2], that when the force probes are applied with differ indentation rates, the measured force is different, whereby for the same amount of indentation, higher forces are obtained under higher indentation rates.

It has further been demonstrated, that when the force probes applied to the eye are tilted or displaced laterally, the relative magnitude of the forces obtained from different probes changes and therefore interferes with the correct interpretation of the data and extraction of IOP [1-2].

It is therefore an object of the present invention to provide systems and methods for measuring IOP using an apparatus that can conforms to the anatomy of the face and therefore can be performed by the patient without professional assistance and eliminate the errors associated with variable position of the indentation.

It is another object of the present invention to provide systems and methods for applying a repeatable force under controlled rate of increase.

It is another object of the present invention to provide systems and methods for interpretation of force data obtained from multiple probes that account for sensor misalignment.

SUMMARY OF THE INVENTION

In accordance with the above objects and those that will be mentioned and will become apparent below, the system for measuring IOP of an eye, in accordance with one embodiment of the invention, generally comprises a device for aligning a tonometry system for eye pressure measurement of a patient, comprising a mask having a contour shape of the patient's face, said mask comprising at least one eye ball opening, said eye ball opening accommodating a plurality of contact probes moveable to contact a surface of the patient's eye ball. In one embodiment the mask has four contact probes per eye ball opening, preferably comprising three outer probes and one central probe. In such embodiment the three outer probes preferably are equally radially spaced from one another. In a preferred embodiment the eye ball opening includes a plurality of separators for preventing rotational misalignment of the tonometry system. In such embodiment, the separators preferably are radially equally spaced from one another. In another embodiment of the invention, the tonometry system includes (i) a plurality of force sensors, the force sensors being adapted to contact a surface of an eye via contact rods of different lengths, (ii) advancing devices for applying gradually increasing forces by advancing the probes towards the eye, (iii) measuring devices for measuring the forces exerted on the force sensors when in contact with the eye surface, and (iv) a processor adapted to receive the measured forces and programmed to determine intraocular pressure (IOP) of the eye as a function of the measured forces.

In one embodiment of the invention, IOP of the eye is determined by plotting the forces measured by two probes on a Cartesian plot and determining the location of a characteristic bend (or intercept) that occurs when both forces attain non-zero value for the first time.

As it will be shown later, the location of this characteristic bend is proportional to the IOP and the relative displacement between the two forces according to the following approximate relationship $$F_E^c = 2k\frac{Z}{d}p \text{ [mmHg]}$$

where:
$F_E^c$ is the measured force on the extended probe E when the retracted probe R is just starting to register a non-zero force, and
Z and d represent vertical and horizontal offsets between the probes E and R, respectively, and
p is the intraocular pressure of the eye, and
k is a proportionality coefficient dependent on the elasticity of the eye.

In one embodiment of the invention, the force sensing unit is detachable from the contact probes, allowing identical sensing units to be used with different contact probes.

In another embodiment of the invention, the force probes are permanently connected to the contact probes and integrated into a custom-fitting unit.

In one embodiment, the system includes a linear transmission device that is adapted to extend and retract force sensors or contact probes.

In some embodiments, the linear transmission device is comprised of a pneumatic bladder operating against a set of springs whereby gradual release of the air in the bladder results in gradual advancement of the probes.

In another embodiment of the invention, the linear transmission device is comprised of a hand-operated plunger compressing a spring against a visco-elastic member. In this embodiment, the relaxation of the stress in the visco-elasticity of the opposing member is responsible for the gradual advancement of the force probes.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE INVENTION

Figure 1:
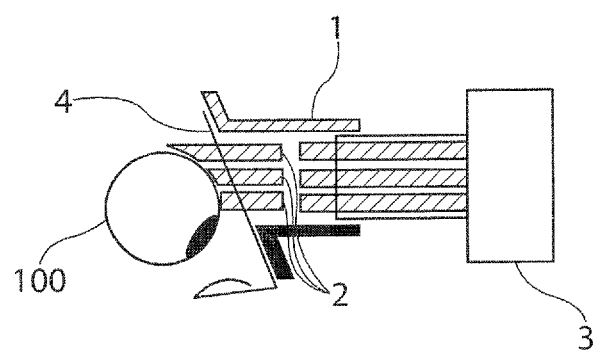
FIG. 1 is diagrammatically illustrates the function of the contact rods or probes of different length providing contact between the tactile tonometer and the human eye.

Before describing the present invention in detail, it is to be understood that this invention is not limited to particularly exemplified methods, apparatus or systems, which, of course, may vary. Thus, although a number of methods and systems similar or equivalent to those described herein can be used in the practice of the present invention, the preferred methods, apparatus and systems are described herein. It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

As used in this specification and the appended claims, the singular forms "a", "an" and "the" include plural referents unless the content clearly dictates otherwise. As such, this statement is intended to serve as antecedent basis for use of such exclusive terminology as "solely", "only" and the like in connection with the recitation of claim elements, or use of a "negative" limitation.

Further, all publications, patents and patent applications cited herein, whether supra or infra, are hereby incorporated by reference in their entirety.

The publications discussed herein are provided solely for their disclosure prior to the filing date of the present application. Nothing herein is to be construed as an admission that the present invention is not entitled to antedate such publication(s) by virtue of prior invention. Further, the dates of publication may be different from the actual publication dates, which may need to be independently confirmed.

DEFINITIONS

In the following description, the terms "probe" "contact probe" and "force sensor" are used interchangeably herein and mean and include a structure that is adapted to contact a surface of an eye, sense the force exerted thereon by the eye, and transmit the sensed force to an associated structure or system such as a processor.

Many aspects of the invention may take the form of a computer-executable instructions, including algorithms executed by a programmable computer. Those skilled in the relevant art will appreciate that the invention can be practiced with other computer system configurations as well. Certain aspects of the invention can be embodied in special-purpose computer or data processor that is specifically programmed, configured or constructed to perform one or more of the computer-executable algorithms described below. Accordingly, the term "computer or "processor" as generally used herein refers to any data processor and includes Internet appliances, hand-held devices (including palm-top computers, wearable computers, multi-processor systems, processor-based or programmable electronics, network computers, minicomputers) and the like.

Some aspects of the invention may also be practiced in distributed computing environments, where tasks or modules are performed by remote processing devices that are linked through a communications network. In a distributed computing environment, program modules or subroutines may be located in both local and remote memory storage devices. Aspects of the invention described below may be stored or distributed on computer-readable media magnetic and optically readable and removable computer disks, fixed magnetic disks, floppy disk drive, optical disk drive, magneto-optical disk drive, magnetic tape, hard-disk drive (HDD), solid state drive (SSD), compact flash or non-volatile memory, as well as distributed electronically over networks. Data structures and transmissions of data particular to aspects of the invention are also encompassed within the scope of the invention.

As stated above and discussed in detail herein, in accordance with one embodiment of the invention, a method for measuring Iop is provided which generally comprises the steps of: (i) providing a palpation system having first and second force sensors, said first force sensor being in a first extended position and said second force sensor being in a first retracted position with respect to the first force sensor, the first and second force sensors being adapted to contact a surface of an eye, a measuring device for measuring the forces exerted on the first and second force sensors when in contact with said eye surface, and a processor adapted to process said measured forces, (ii) placing the palpation system on a surface of the eye, whereby the extended first force sensor is in contact with the eye surface, (iii) applying a gradual first force to the eye surface with the palpation system and measuring the force exerted on the first force sensor until the retracted second force sensor contacts the eye surface, whereby the second force sensor measures a first non-zero force value, and (iv) determining IOP of the eye as a function of the force exerted on the first force sensor when the second force sensor contacts the eye surface.

In another embodiment of the invention, the method for determining (IOP) of an eye, comprises the steps of: (i) providing a palpation system having first and second force sensors, a measuring device measuring the forces exerted on the first and second force sensors when in contact with the eye surface, and a processor adapted to process the measured forces, (ii) placing the palpation system on a surface of the eye, whereby at least one of the first and second force sensors is in contact with the eye surface, (iii) subjecting the first and second force sensors to a first palpation sequence comprising preprogrammed extension and retraction of each force sensor, (iv) measuring a first plurality of forces exerted on the first force sensor and a second plurality of forces exerted on the second force sensor over a first period of time and at a plurality of TOP values during the palpation sequence, (v) generating a plurality of calibration curves from the measured first and second plurality of forces, and (vi) determining IOP of the eye based on the generated plurality of calibration curves.

The contoured facial mask with multiple contact probes for use with tactile tonometer will now be described in detail. As will be apparent from the following description, the systems and methods of the invention substantially reduce or eliminate the disadvantages and drawbacks associated with convention systems and methods for measuring characteristics associated with an eye; particularly, IOP.

Referring first to FIG. 1, there is shown one embodiment of the contoured facial mask system (denoted generally "1"), which, in the illustrated embodiment, is placed onto the face of the user 4.

As illustrated in FIG. 1, the system 1 comprises several, for example four, movable contact rods 2 (FIG. 2) one end of which is shaped such as to conform to the contour of the eye and eye lid 100, while the other end is flat allowing for intimate contact with a force measuring unit 3, also referred to as "tactile tonometer".

As further illustrated in FIG. 1, the length of each contact rod 2 may be different.

Figure 3A:
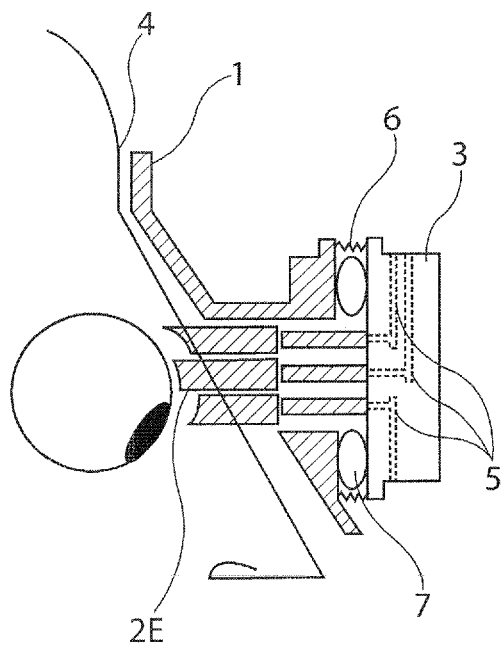
FIG. 3A is a view similar to FIG. 1 illustrating a conformal facial mask with moveable contact rods or probes where at least one of the movable rods or probes extends past the others in accordance with the present invention.

According to the invention, to contour mask system 1 preferably includes at least one probe that is longer than the rest, labeled 2E in FIG. 3A.

Figure 3B:
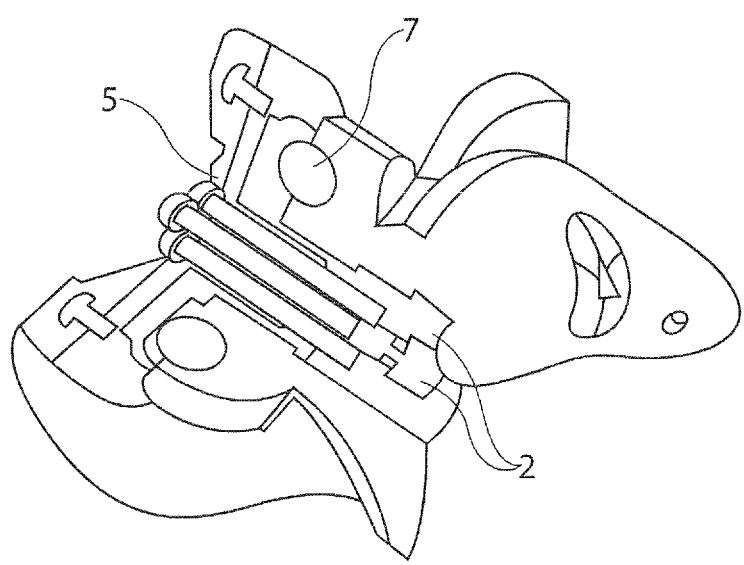
FIG. 3B is perspective view of a pneumatically-driven contoured tactile facial mask in accordance with the present invention.
Figure 3C:
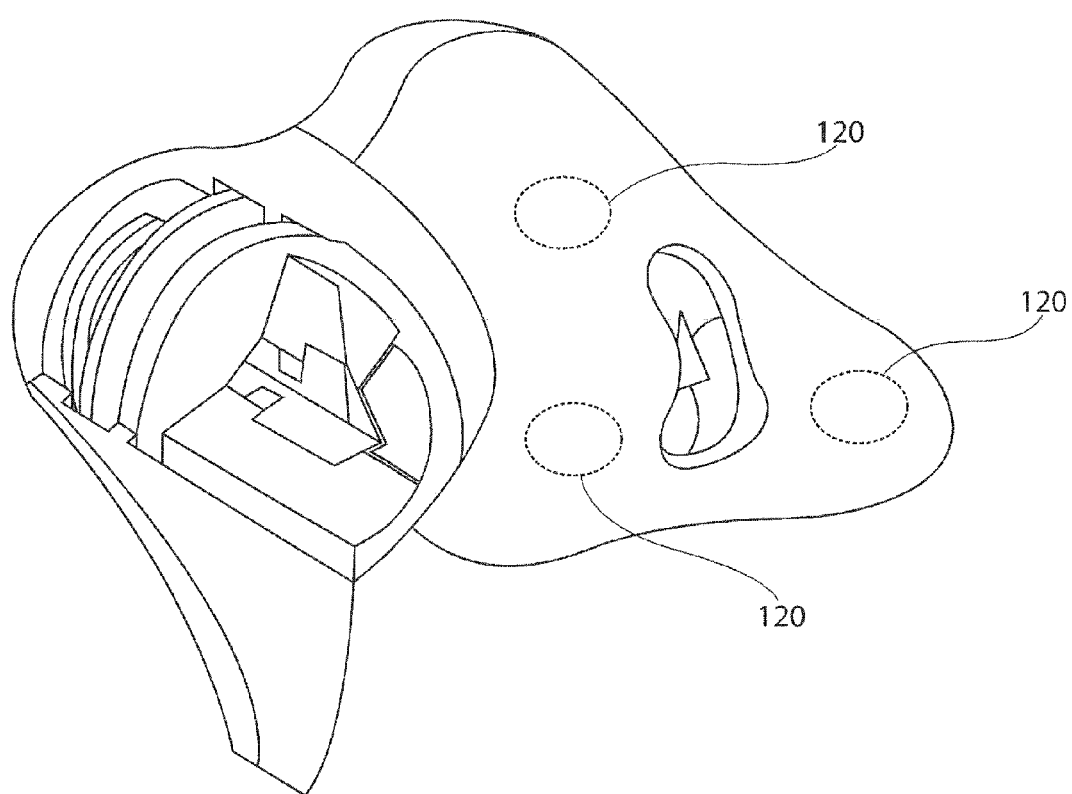
FIG. 3C is perspective view of a spring-driven contoured tactile facial mask in accordance with the present invention
Figure 3D:
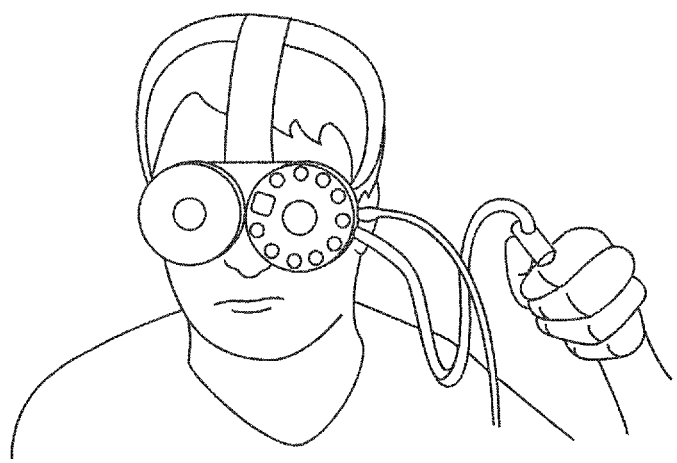
FIG. 3D is front view of a pneumatically-driven contoured tactile facial mask shown in FIG. 3B, worn on a person.
Figure 4:
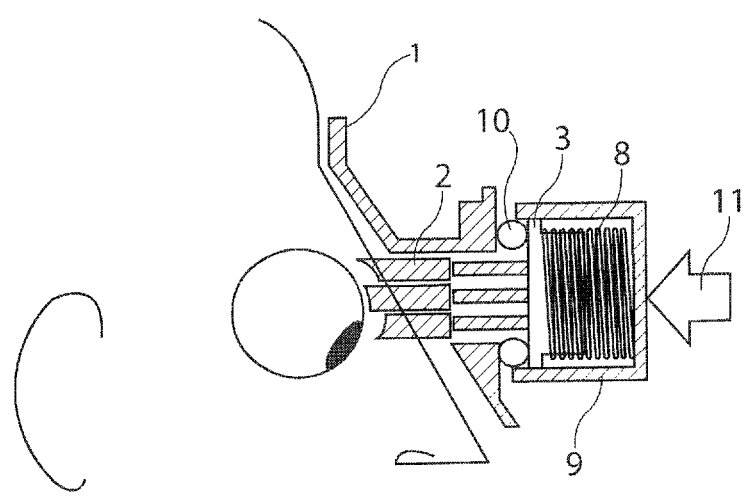
FIG. 4 is a view, similar to FIG. 1 and FIG. 3C, illustrating a conformal facial mask with moveable contact rods advanced towards the face/eye under the action of a preloaded spring in accordance with the present invention.

In a preferred embodiment, the system 1 further includes a translation stage comprised of pneumatic bladder 7 acting against two or more springs 6 as shown in FIGS. 3A and 3B. Alternatively, spring 6 make take the form of resiliently deformable foam as shown in FIGS. 3C and 4.

Translating the tonometer 3 away from the eye is performed by pressurizing the bladder 7, while advancing it towards the eye is performed by releasing the pressure in bladder 7.

In one embodiment of the tactile contoured mask, the tonometer contains cantilevered force sensors 5, which are in contact with the contact rods 2 via extension rods 2E.

In another embodiment of the contoured facial mask, the tactile tonometer 3 is advanced towards the eye by an operator pressing on a cap 9 at location 11 (see FIG. 4), which in turn compresses spring 8 by a pre-set distance H towards the mask 1. The compression distance sets a nearly constant spring force which is balanced by a visco-elastic compression ring 10. Gradual collapse (stress relaxation) in the viscoelastic ring 10 results in advancing the tactile tonometer 3 towards the eye following an exponential time series.

In a preferred embodiment, the length of contact probes 2 is selected such, that prior to depressing cap 9, the contact probes are retracted a set distance into the mask 1. (see FIG. 7). This distance is equal to the instantaneous displacement the visco-elastic body 10 will undergo under the action of the force of the compressed spring 8.

Figure 6A:
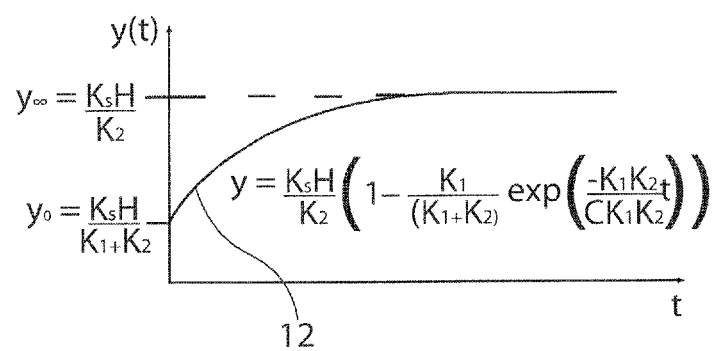
FIGS. 6A and 6B are graphs illustrating the logarithmic law of advancement of the force sensors driven by a spring in accordance with the present invention.

Upon depressing cap 9, the tactile tonometer 3 will advance instantaneously a set distance shown as $y_0$ in FIG. 6A. Subsequently, the tonometer 3 will travel according an exponential curve 12 with diminishing velocity 13.

Figure 5:
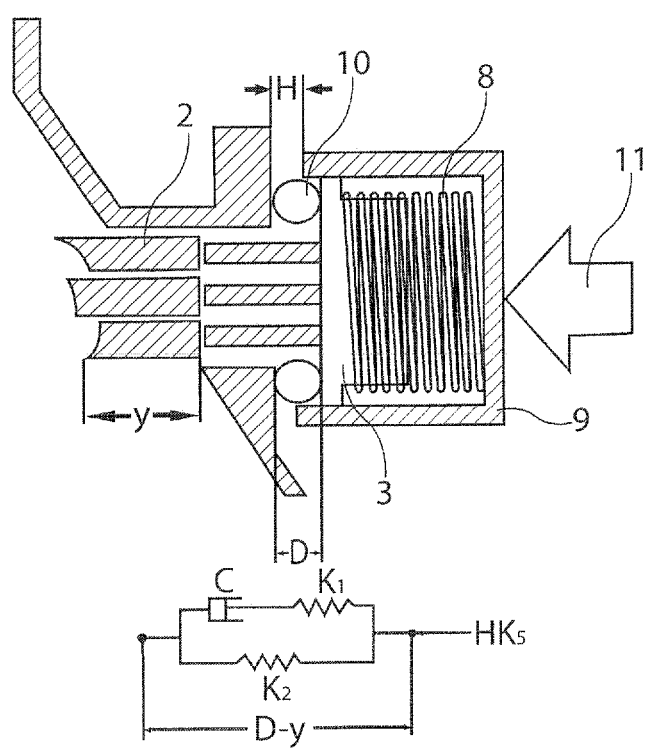
FIG. 5 is a view, similar to FIG. 1 and FIG. 3C, illustrating a tactile tonometer with a manual indentation rate-controlling apparatus in accordance with the present invention.

FIG. 5 illustrates one embodiment of manual palpation in accordance with the present invention. The user applies a force F at location (11) until gap H closes. Since the stiffness of the spring (8) can be selected to be much smaller than the stiffness of the viscoelastic member (10), the compression of (8) will result in a relatively constant force $F_0 = K_S H$. The viscoelastic member (10) will start deforming under the action of the force F following the laws of viscoelasticity. The initial thickness, D, of member (10) will be rapidly reduced by an amount $y_0 = F_0/(K_1 + K_2)$, which will be equal to the instantaneous advancement of probes (2). Subsequently, according to the Maxwell model of viscoelastic bodies depicted in (12), the advancement will proceed according to an exponential law $$y = \frac{K_S H}{K_2} \left(1 - \frac{K_1}{(K_1 + K_2)} \exp\left(\frac{-K_1 K_2}{C K_1 K_2} t\right)\right)$$

depicted in FIG. 6A.

Figure 6B:
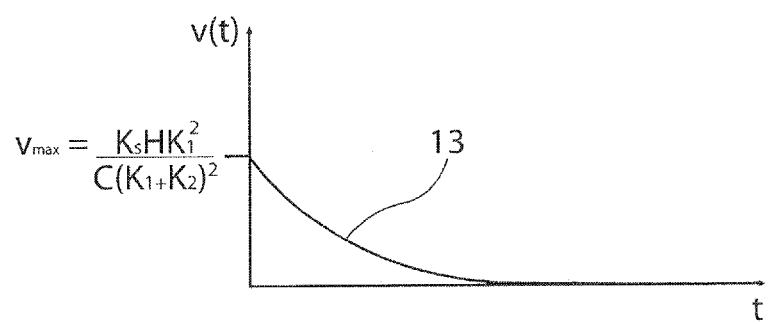

FIG. 6 illustrates the logarithmic law of advancement of the force sensors driven by a spring with a stiffness $K_S$, compressed by amount H and controlled by a viscoelastic member (10) with viscoelastic material constants $K_1$, $K_2$, and C. Displacement of force sensors vs. time is shown in FIG. 6A—trace (12) and velocity of force sensors is shown in FIG. 6B—trace (13)

Figure 7:
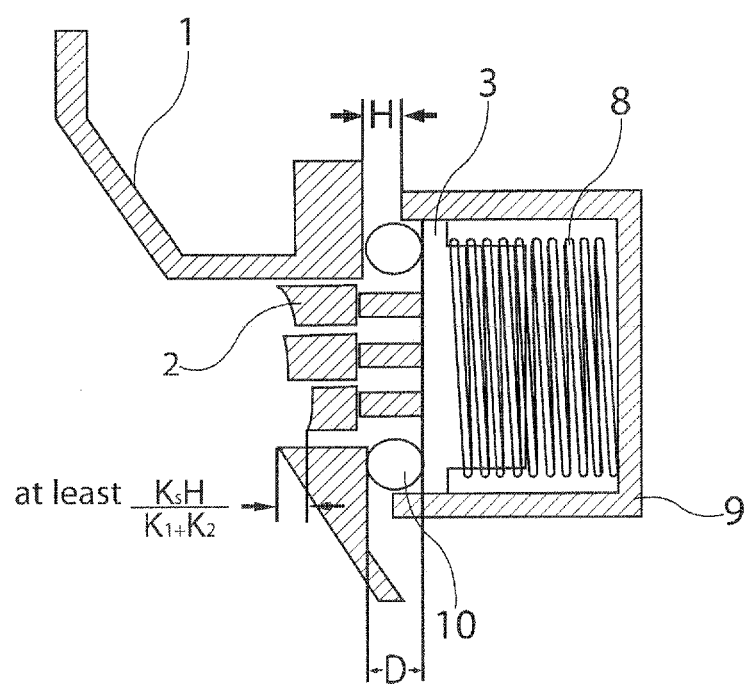
FIG. 7 is a view, similar to FIG. 1, of a force probe in a retracted position in accordance with the present invention.

FIG. 7 illustrates the desired retracted position of force probe intend to ensure that when cap (9) is pressed by distance H, the instantaneous advancement of probes (2) will occur prior to contacting the eye. The retracted distance should be at least $K_S H/(K_1+K_2)$, which can be adjusted by choosing the length of the movable probes (2). The parameter $K_S$ is the stiffness of spring (8), and $K_1$, $K_2$ are the stiffness coefficients of viscoelastic member (10).

Figure 8:
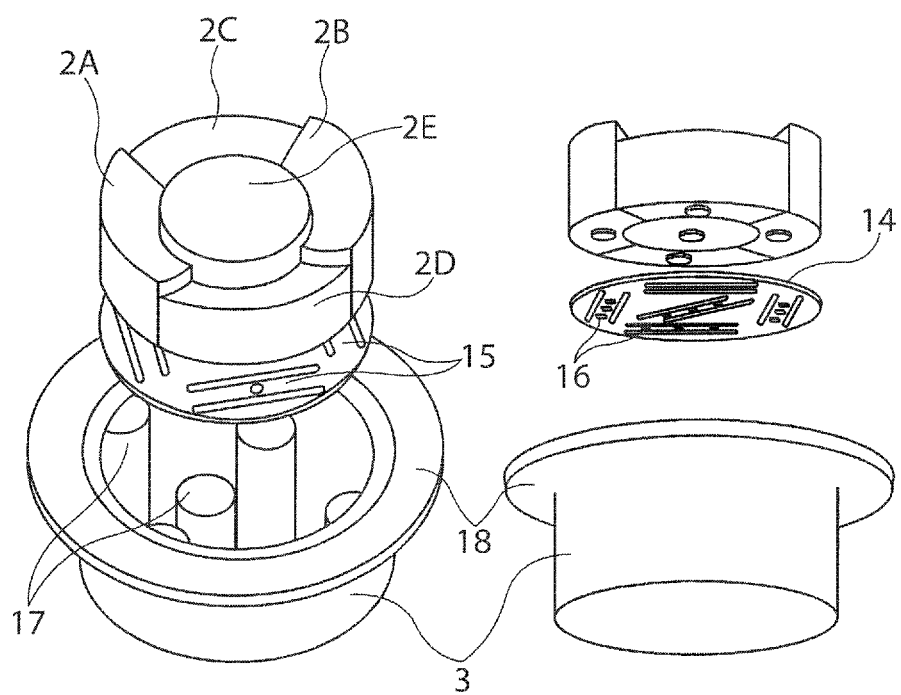
FIG. 8 is a perspective/exploded view of a tactile tonometer force sensor assembly in accordance with the present invention.

Referring now to FIG. 8, there is shown another embodiment of a mechanical palpation system of the invention. In this embodiment, the contact probes 2 are integrated into the tactile tonometer 3 and comprise a single unit capable of translating to and away from the eye.

As illustrated in FIG. 8, probes 2 are preferably attached to a flat spring plate 14. In one embodiment of the invention, the plate 14 contain slots that delineate flexible strips 15. Each of the strips 15 contains at least one strain gauge 16 attached to the strip and capable of measuring elastic strains.

In accordance with one embodiment of the invention, during mechanical palpation with the system, the contact probes 2 will indent the flexible strips 15, and the applied force will be measured by strain gauges 16.

To eliminate cross-talk between neighboring strips, plate 14 is supported by several support pillars 17 also part of the tactile tonometer 3. According to this embodiment of this sensor assembly, the housing 3 has a rim 18 providing support for spring 8 and viscoelastic member 10 (FIG. 4), or pneumatic member 7 (FIG. 3A).

Figure 9:
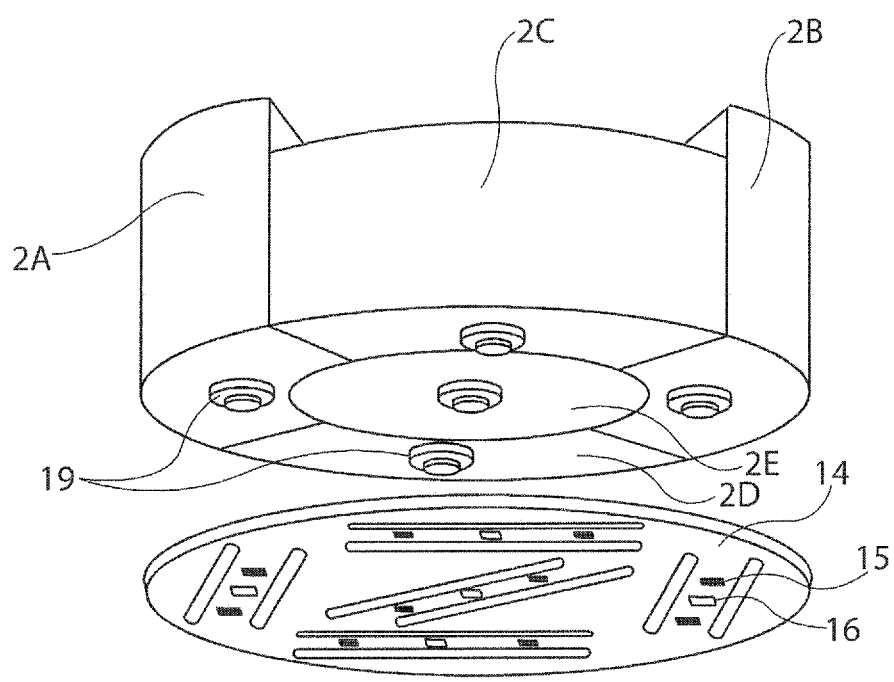
FIG. 9 is a view similar to FIG. 8 showing details of a portion of the force sensor assembly of FIG. 8.

Referring also to FIG. 9, the underside of probes 2A, 2B, 2C, 2D, 2F contain an alignment stand-off tabs 19 intended to provide indentation of the central portion of each elastic strip 15. Flexing of the strips 15 is detected by the strain in strain gauges 16.

As previously reported by us in [1-2], the eye can be modeled as a vessel with visco-elastic walls filled by incompressible fluid. When the volume of the fluid is increased, the vessel walls stretch and exert compressive forces onto the fluid known as intraocular pressure. Conversely, the vessel walls are under tension T inducing the required stretch. When indented by the tactile probes, the shape of the vessel walls change, so that equilibrium is established between the tension in the deformed vessel walls and the force probes indenting it.

According to the present invention, the force analysis of during tactile tonometery is approximated via an abstract one-dimensional string model, where the tension in the string is proportional to the IOP, while its shape is modified by the action of the external force probes. While the approach is not an exact representation of the contact problem, it captures essential geometric features of the tactile tonometer that provide a clear quantitative method to interpret the observed forces during palpation.

Figure 10:
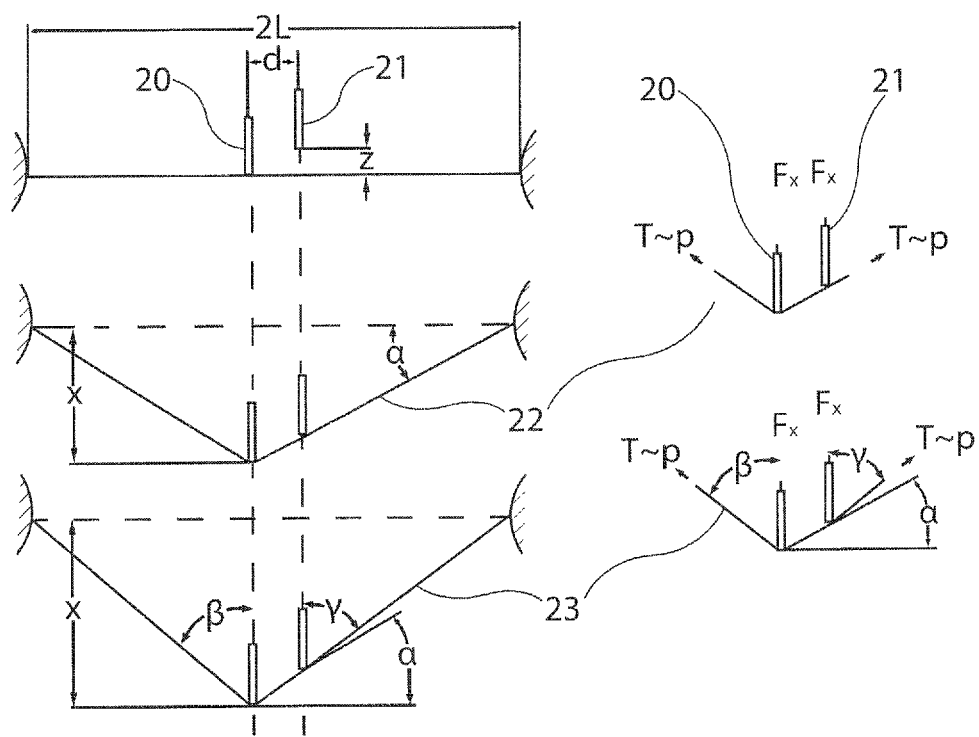
FIG. 10 represents a mechanical model of pressure measurement by two offset probes in accordance with the present invention.

FIG. 10, represents a mechanical model of pressure measurement by two offset probes, that explains the observed tactile forces qualitatively.

According to the present invention, IOP (p) can be determined in proportion to the tension force T in an elastic by the following relationship:

$$p = T/k \text{ [mmHg]} \qquad \text{Eq. 1}$$

where p is the intraocular pressure, and k is the elastic coefficient of an imaginary string representing the elasticity of the sclera. It should be noted that the Eq. 1 conforms to a thin-walled vessel model where the pressure inside the vessel is proportional to the stress in the walls. If a thin section of a spherical vessel is cut along a meridian curve, one will obtain a circular string stretched with tensile force T. Therefore, while abstract, Eq. 1 does have physical origins.

Considering a short segment of the circular string as a straight string with length 2L, under tension T, one obtains the starting configuration in FIG. 10.

The string from FIG. 10 is indented by two probes 20 and 21 offset vertically and horizontally by distances Z and d, respectively.

Advancing probes 20 and 21 downward leads to a non-zero force registered by the extended probe 20, while probe 21 will measure zero until both probes reach configuration 22.

The model is obtained by analogy with a thin elastic string under tension T, proportional to the intraocular pressure p inside the eye. Initially, only the extended probe (20) measures a force until the deformation of the string reaches an angle α determined by the mutual positions of the two probes (20) and (21) as illustrated in configuration (22), i.e. tan α=Z/d. Further indentation by the two probes results in increasing forces measured by both probes as in configuration (23)

According to the invention, the force measured by probe 20 ($F_E$) and 21 ($F_R$) can be obtained from:

$$F_E = T\left(\frac{x}{\sqrt{\left(L-\frac{d}{2}\right)^2 + x^2}} + \frac{x}{\sqrt{\left(L+\frac{d}{2}\right)^2 + x^2}}\right) \quad \text{Eq. (2)}$$

for $x \le (L + d/2)\tan\alpha$.

for $x \le (L+d/2)\tan\alpha$.     Eq. (2)

$F_R = 0$ where $\tan\alpha = Z/d$.

Further advancement of probes 20 and 21 leads to non-zero forces measured by the probes according to:

$F_E = T(\cos\beta + \sin\alpha)$ $F_R = T(\cos\gamma - \sin\alpha)$ for $x > (L+d/2)\tan\alpha$     Eq. (3)

where $$\cos\beta = \frac{x}{\sqrt{\left(L-\frac{d}{2}\right)^2 + x^2}};$$     Eq. (4)

$$\cos\gamma = \frac{x-Z}{\sqrt{\left(L-\frac{d}{2}\right)^2 + (x-Z)^2}};$$

$$\sin\alpha = \frac{Z}{\sqrt{d^2 + Z^2}}.$$

In the limiting case of configuration 22, $F_R$=0, which from Eq. (4) is equivalent to $\cos\gamma = \sin\alpha$     Eq. (5)

or $$x = (L+d/2)\tan\alpha = Z + \frac{Z}{d}(L - d/2)$$     Eq. (5A)

Substituting Eq. (5A) into Eq. (2) provides the limiting force in the extended probe 20. A simple approximation in the case when L>>d/2 yields $$F_E^c \approx 2T\tan\alpha = 2T\frac{Z}{d}$$     Eq. (6)

Combining Eq. (6) with Eq. (1) shows that in the limiting configuration 22 (FIG. 10) when $F_R$=0, the extended probe 20 measures a force proportional to the intraocular pressure and the ratio Z/d $$F_E^c = 2k\frac{Z}{d}p$$     Eq. (7)

According to this invention, application of Eq. (7) allows one to determine the unknown coefficient 2k using a single measurement at a known pressure p and ratio Z/d.

Furthermore, Eq. (7) can be used to determine if a sensor is misaligned, which would result in different Z/d ratio. Since at a given pressure, all force intercepts are proportional to a specific Z/d ratio, any change in the relative magnitude of one of the intercepts in comparison to the rest, would indicate misalignment of the sensor. This information can be used to either correct for the misalignment, or rejecting the measurement result and acquiring a new one.

EXAMPLES

The following examples are given to enable those skilled in the art to more clearly understand and practice the present invention. They should not be considered as limiting the scope of the invention, but merely as being illustrated as representative thereof.

Example 1

Design of Manual Indentation Rate-Controlling Apparatus Advancement Mechanism for Controlled Indentation Rate As described in this invention, a manually controlled indentation mechanism can be designed to provide the required indentation rate control for the tactile tonometer. As illustrated in FIG. 5, when cap 9 is compressed by a distance H, the resulting spring force is $F_0=K_S H$. This force compresses the visco-elastic spacer 10, which is can be a donut-shaped open-cell polyurethane foam. Open cell-polyurethane foams can be described by a three-parameter Maxwell viscoelastic bodies [4]. A wide variety of visco-elastic foams, also known as shape-memory foams, are available on the market including Sorbothane, polynorbornene, Noene, Astro-sorb, and Neoprene.

By selecting a visco-elastic member with viscoelastic material constants $K_1$ [units N/m], $K_2$ [units N/m], and C [units N-s/m], it can be shown that the mechanical model depicted in FIG. 5B will result in exponential time-response of the tonometer 3 (FIG. 5A) according to the following equation:

$$y(t) = \frac{K_S H}{K_2}\left(1 - \frac{K_1}{(K_1+K_2)}\exp\left(\frac{-K_1 K_2}{C K_1 K_2}t\right)\right)$$     Eq. (8)

A sketch of the displacement y(t) is shown in FIG. 6A. As can be seen the tonometer 3 will undergo an instantaneous deflection $$y_0 = \frac{K_S H}{K_1 + K_2},$$

which implies that the force probes 2 need be retracted by distance prior to compression of cap 9 as shown in FIG. 7.

FIG. 6B illustrates the time derivative of Eq. (9). As one can see, the maximum velocity is obtained at the beginning of the motion according to $$v_{max} = \frac{K_S H K_1^2}{C(K_1 + K_2)^2} \qquad \text{Eq. (9)}$$

By choosing a foam with sufficiently large damping coefficient C, the advancement velocity can be kept under 1 mm/sec as which has been found to be optimal [2].

Example 2

Calibration of Tactile Tonometer Using Multiple Probes and a Single IOP Value

In clinical practice, it is anticipated that each human subject will have a different eye size, with variable eyelid thickness and elasticity. Therefore, tactile tonometers will need a calibration against an independent measurement of the IOP. Since in practice the eye pressure of a human subject cannot be adjusted at will, it is advantageous to be able to calibrate the unit from a single known value of the IOP. The following example illustrates how data from several force probes can be used to determine the calibration coefficients of each from a single measurement.

Figure 11:
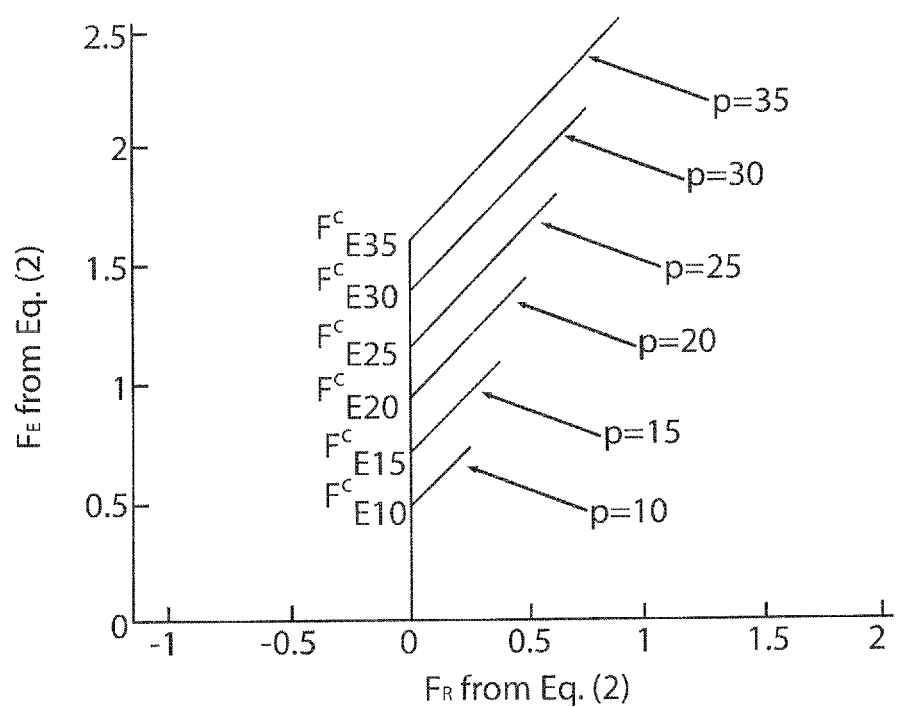
FIG. 11 is a graph of force measured by two offset probes $F_E$ and $F_R$ at various pressures.

As described in this invention, when forces from two probes are plotted against each other, the resulting curve exhibits a sharp change of slope at a point determined by Eq. (7). FIG. 11 shows $F_E$ verses $F_R$ and illustrates the location of this point labeled by $F_{E10-35}^c$ for pressure levels p=10, 15, 20, 25, 30 and 35 mmHg.

When two force probe pairs are used (a total of 3 probes) with known but different distance ratios $Z_1/d_1$ and $Z_2/d_2$, it is possible to obtain two calibration curves. For example, instead of carrying out an experiment at pressure 2p, one might use $Z_2/d_2 = 2Z_1/d_1$. According to Eqs. (3) and (7) the resulting force curve will be equivalent to one obtained from probe pare with ration $Z_1/d_1$ but at pressure 2p. Therefore, using multiple probe pairs, one can obtain calibration curves similar as if the experiment was carried out at different pressures.

In order to obtain an absolute pressure reading, at least one pressure should be known. From it, the unknown subject-specific coefficient 2k can be obtained according to $$2k = \frac{F_{E1}^c}{p} \frac{d_1}{Z_1} \qquad \text{Eq. (10)}$$

Based on Eq. (10) evaluated at single pressure p, the subject-specific calibration factor 2k can be determined for subsequent use. Therefore this method allows calibration of the tactile tonometer using a single experiment that collects data from several force pairs. The true intraocular pressure for this experiment can be obtained from Goldmann applanation tonometer.

It is apparent that this application requires at least 3 force probes. An example of such arrangement is shown in FIG. 8 probes 2A-B offset from 2E at a given distance, and probes 2C-D offset from 2E at another distance.

Example 3

Fabrication of Contoured Facial Masks

Fabricating of contoured masks conforming to the facial anatomy of a subject can be accomplished by first scanning the face using commercial laser or optical 3D scanner.

Figure 2:
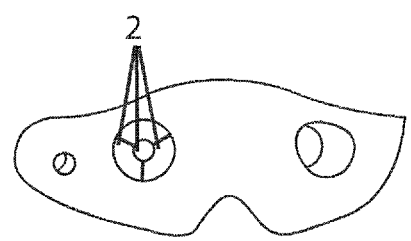
FIG. 2 is a perspective view of contoured facial mask with multiple contact rods or probes in accordance with one of the present invention.

A mask with embedded probes can then be printed using stereo-lithography (3D printing as illustrated in FIG. 2. Alternatively, a mask may be custom fitted to an individual using a plurality of built-in inflatable air bags shown in phantom at 120 in FIG. 3C.

A pneumatically driven tactile mask is shown in FIG. 3A-C.

As will readily be appreciated by one having ordinary skill in the art, the present invention provides numerous advantages over hand-held tactile tonometers and methods for measuring IOP. Among the advantages are the following:

The contoured facial mask and its components improves the repeatability of the measurements and reduces alignment errors.

The contoured facial mask and its components aids the user in self-administering IOP measurement.

The contoured facial mask and its components provides repeatable indentation and repeatable control of the rate of application of the indentation.

The contoured facial mask and its components eliminate the need for motorized more expensive indentation mechanisms.

The provision of IOP measuring systems and methods that utilize a miniaturized and integrated multi-force sensor based on integrated strain gauges.

The invention also demonstrates that the calibration of the tactile tonometer can be carried out using a single know pressure followed by the application of the tactile tonometer.

Without departing from the spirit and scope of this invention, one of ordinary skill can make various changes and modifications to the invention to adapt it to various usages and conditions. By way of example, the force sensors or contact probes may be formed of ferromagnetic materials which will allow them to snap onto magnets embedded into the mask, thus making a quick-release version and permitting use of probes with different lengths which may be rotatable so that they interchange places. As such, these changes and modifications are properly, equitably, and intended to be, within the full range of equivalence of the following claims.

REFERENCES

[1] Polyvas, P. Madarasz, M, and Enikov ET. "Development of Tactile Eye Stiffness Sensor," Journal of Experimental Mechanics, pre-print available September 2012

[2] Eniko Enikov; Peter Polyvas; Gholam Peyman, "Trans-scleral tactile tonometry: An instrumented approach," Medical Engineering and Physics, pre-print available September 2012.

[3] "Eye Tonometry Apparatus, Systems, and Methods", Inventors: Enikov E. T. and Peyman, G. U.S. Pat. No. 7,959,570 B2, Jun. 14, 2011.

[4] N. J. Mills, "Finite Element Models for the Viscoelasticity of open-cell polyurethane foam," Cellular Polymers, v. 25, (5), 2006.

What is claimed is:

1. A system for measuring intraocular pressure (IOP) of a subject's eye, comprising:
   a plurality of force sensors, said force sensors being adapted to contact a surface of the subject's eye via moveable probes;
   an advancing device for advancing said force sensors towards the subject's eye in a controlled fashion;
   a measuring device for measuring forces being exerted on said force sensors when said force sensors are in contact with the subject's eye surface; and
   a processor adapted to receive said measured forces and programmed to determine intraocular pressure (IOP) of the subject's eye as a function of said measured forces, wherein said IOP of the subject's eye is determined by finding intercepts of force curves with either vertical or horizontal axes, where a distance of said intercepts is proportional to intraocular pressure and an offset between the two force probes via the following relationship $$p = \frac{d}{2kZ} F_E^c \text{ [mmHg]}$$

where:
p is the IOP value, and
d represents a horizontal distance and Z represents a vertical distance, respectively, between the force probes,
k is a calibration stiffness coefficient with units of mm$^2$, and
$F_E^c$ is the distance from the intercepts to the origin of the plot where both forces are zero.

2. The system of claim 1, wherein said system includes a linear force sensor transmitter that is adapted to extend and retract each of said force sensors.

3. The system of claim 2, wherein said linear force sensor transmitter is further adapted to secure said force sensors in extended and retracted positions.

4. The system of claim 1, wherein said force sensors include a plurality of different length rods.

5. The system of claim 4, wherein a distal end of at least one of said rods is contoured to approximate a shape of the subject's eye.

6. The system of claim 4, wherein a distal end of one of said rods extends beyond distal ends of the other rods.

7. The system of claim 1, wherein said advancing device includes a spring.

8. The system of claim 1, wherein said advancing device includes resiliently deformable foam.

9. A method for measuring intraocular pressure IOP of a subject's eye, comprising the steps of:
   providing a palpation system as claimed in claim 1, having first and second force sensors with a known Z/d offset ratio. said force sensors being adapted to contact a surface of the subject's eye, where the first force sensor contacts the subject's eye first followed by the second sensor,
   measuring forces exerted on said first and second force sensors when said first and second force sensors are in contact with the subject's eye surface, and processing said measured forces;
   applying a gradual force to the subject's eye surface with said palpation system and measuring force exerted on said first and second force sensors until both force sensors measure non-zero force;
   determining a force value of said first force sensor when said second sensor contacts the subject's eye and registers a first non-zero force, and
   determining a calibration stiffness coefficient k calibration coefficient from $$2k = F_{E1}^c/p \; d_1/Z_1,$$

where:
p is the IOP value, and
d represents a horizontal distance and Z represents a vertical distance, respectively, between the force probes,
$F_E^c$ is the measured force value of said first sensor when said second sensor contacted the subject's eye.

10. The method of claim 9, where said first and second force probes have different known Z/d ratios, whereby the resulting force curves are interpreted as if obtained at different pressures.

11. The system of claim 1, wherein the moveable probes are contained in a facial mask.

12. The method of claim 10, wherein the fore curve from the force pair Z/d, is interpreted as a force curve obtained from the first pair $Z_1/d_1$, but under pressure $p_2 = p$, $Z_2 d_1/d_2 Z_1$.

13. A system for measuring intraocular pressure (IOP) of a subject's eye, comprising:
   a plurality of force sensors, said force sensors being adapted to contact a surface of the subject's eye via moveable probes contained in a facial mask;
   an advancing device for advancing said force sensors towards the subject's eye in a controlled fashion;
   a measuring device for measuring forces being exerted on said force sensors when said force sensors are in contact with the subject's eye surface; and
   a processor adapted to receive said measured forces and programmed to determine intraocular pressure (IOP) of the subject's eye as a function of said measured forces, wherein said IOP of the subject eye is determined by finding intercepts of force curves with either vertical or horizontal axes, where a distance of said intercept is proportional to intraocular pressure and an offset between the two force probes via the following relationship $$p = \frac{d}{2kZ} F_E^c \text{ [mmHg]}$$

where:
p is the IOP value, and
d represents a horizontal distance and Z represents a vertical distance, respectively between the force probes,
k is a calibration stiffness coefficient with units of mm$^2$, and
$F_E^c$ is the distance from the intercepts to the origin of the plot where both forces are zero, wherein said mask has a plurality of inflatable bags for custom fitting the mask to conform to a facial anatomy of the subject.

14. The system of claim 13, wherein the advancing device includes a spring or resiliently deformable foam.

15. The system of claim 13, wherein said system includes a linear force sensor transmitter that is adapted to extend and retract each of said force sensors.

16. The system of claim 13, wherein said linear force sensor transmitter is further adapted to secure said force sensors in extended and retracted positions.

17. The system of claim 13, wherein said force sensors include a plurality of different length rods.

18. The system of claim 17, wherein a distal end of at least one of said rods is contoured to approximate a shape of the subject's eye.

19. The system of claim 17, wherein a distal end of one of said rods extends beyond distal ends of the other rods.

\* \* \* \* \*